US011324556B2

(12) United States Patent
Turgeman et al.

(10) Patent No.: US 11,324,556 B2
(45) Date of Patent: May 10, 2022

(54) COMBINING CATHETER VISUALIZATION FROM DIFFERENT COORDINATE FRAMES

(71) Applicant: Biosense Webster (Israel) Ltd., Yokneam (IL)

(72) Inventors: Aharon Turgeman, Zichron Ya'acov (IL); Avigdor Rosenberg, Kiryat Tivon (IL); Uri Yaron, Zichron Ya'acov (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 531 days.

(21) Appl. No.: 16/215,893

(22) Filed: Dec. 11, 2018

(65) Prior Publication Data
US 2020/0179057 A1 Jun. 11, 2020

(51) Int. Cl.
*A61B 34/20* (2016.01)
*A61B 90/00* (2016.01)
(Continued)

(52) U.S. Cl.
CPC .............. *A61B 34/20* (2016.02); *A61B 5/062* (2013.01); *A61B 18/1492* (2013.01);
(Continued)

(58) Field of Classification Search
CPC ......... A61B 34/20; A61B 90/37; A61B 5/062; A61B 18/1492; A61B 2034/2051;
(Continued)

(56) References Cited

U.S. PATENT DOCUMENTS

| 5,391,199 A | 2/1995 | Ben-Haim |
| 6,239,724 B1 | 5/2001 | Doron et al. |

(Continued)

FOREIGN PATENT DOCUMENTS

WO     9605768 A1     2/1996

OTHER PUBLICATIONS

Extended European search report for corresponding European patent application No. 19214706.4, dated Mar. 10, 2020.

*Primary Examiner* — Bill Thomson
*Assistant Examiner* — Delia M. Appiah Mensah
(74) *Attorney, Agent, or Firm* — Notaro, Michalos & Zaccaria P.C.

(57) ABSTRACT

In one embodiment, a medical probe tracking system includes a first probe, a magnetic field generator to generate a magnetic field, and processing circuitry to measure first electrical currents between body surface electrodes and first probe electrodes, receive magnetic position signals from a magnetic field sensor of a second probe, compute first position coordinates of the first probe in a first coordinate frame responsively to distribution of the first electrical currents, render an initial 3D representation of the first probe in the first coordinate frame and then compute a current-position map with respect to a second coordinate frame defined by the magnetic field generator, find a transformation between the first and second coordinate frames, apply the transformation to the first position coordinates yielding second position coordinates, and render a modified 3D representation of the first probe according to the second position coordinates in the second coordinate frame.

6 Claims, 11 Drawing Sheets

(51) Int. Cl.
*A61B 5/06* (2006.01)
*A61B 18/14* (2006.01)
*G16H 30/40* (2018.01)

(52) U.S. Cl.
CPC .............. *A61B 90/37* (2016.02); *G16H 30/40* (2018.01); *A61B 5/063* (2013.01); *A61B 5/066* (2013.01); *A61B 2034/2051* (2016.02); *A61B 2034/2065* (2016.02); *G06T 2210/41* (2013.01)

(58) Field of Classification Search
CPC . A61B 2034/2065; A61B 5/066; A61B 5/065; A61B 2018/1467; A61B 2018/00351; A61B 2018/00595; A61B 5/063; G16H 30/40; G06T 2210/41
See application file for complete search history.

(56) References Cited

U.S. PATENT DOCUMENTS

| | | |
|---|---|---|
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 7,756,576 B2 | 7/2010 | Levin |
| 7,848,787 B2 | 12/2010 | Osadchy |
| 7,869,865 B2 | 1/2011 | Govari et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2007/0135803 A1 | 6/2007 | Belson |
| 2011/0238083 A1 | 9/2011 | Moll et al. |
| 2012/0150022 A1* | 6/2012 | Bar-Tai ................. A61B 5/063 600/424 |
| 2012/0172702 A1 | 7/2012 | Koyrakh |
| 2012/0265054 A1* | 10/2012 | Olson ................... A61B 5/063 600/424 |
| 2013/0066193 A1 | 3/2013 | Olson |
| 2014/0095105 A1 | 4/2014 | koyrakh et al. |
| 2016/0367168 A1 | 12/2016 | Malinin et al. |
| 2017/0065353 A1* | 3/2017 | Ludwin ................. A61B 5/063 |
| 2017/0209072 A1 | 7/2017 | Oren |
| 2017/0354339 A1* | 12/2017 | Zeidan .................. A61B 5/065 |
| 2018/0137687 A1 | 5/2018 | Katz |
| 2018/0182157 A1 | 6/2018 | Zar et al. |
| 2019/0340838 A1* | 11/2019 | Gluhovsky ............ G06T 19/20 |
| 2019/0350489 A1* | 11/2019 | Rosenberg ........... A61B 5/6853 |

* cited by examiner

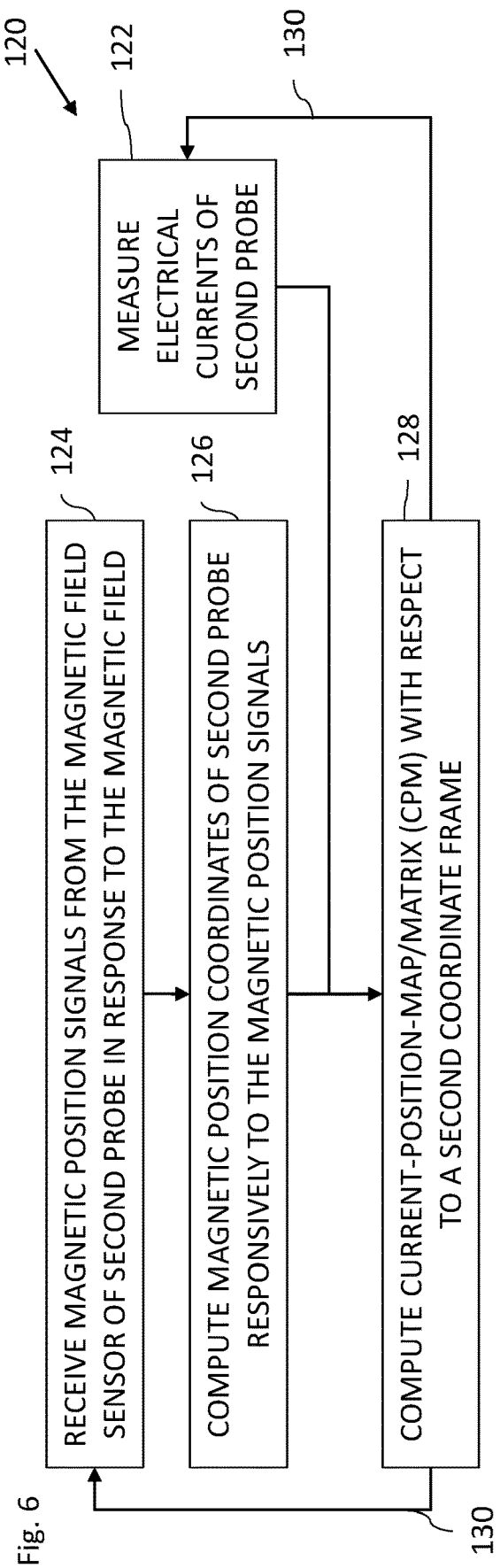
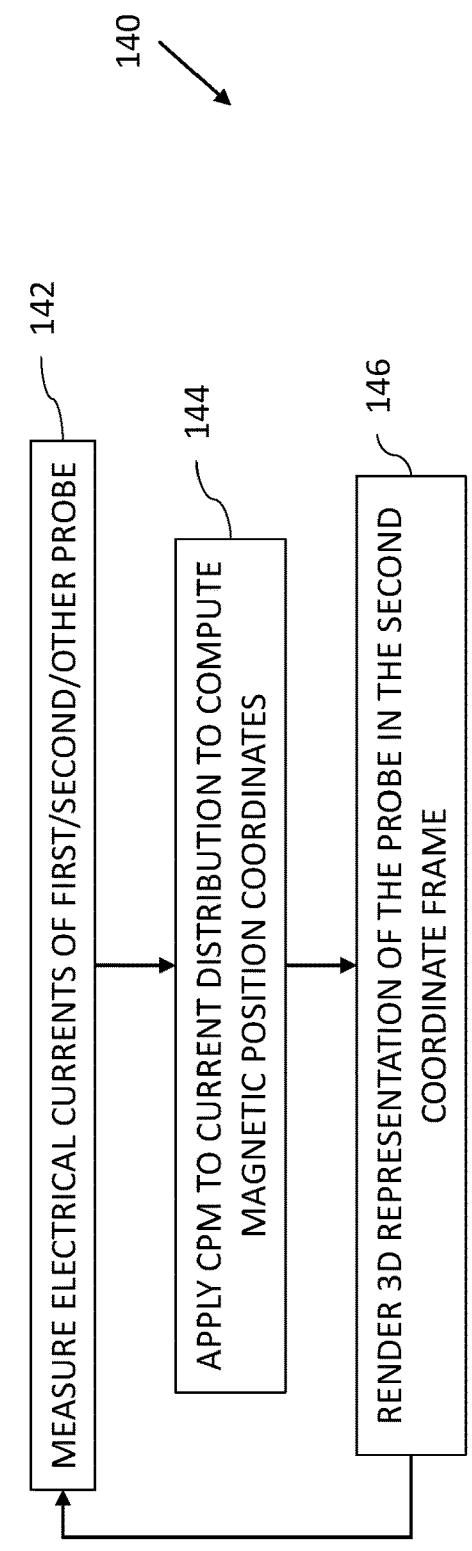
Fig. 6
Fig. 7

COMBINING CATHETER VISUALIZATION FROM DIFFERENT COORDINATE FRAMES

FIELD OF THE INVENTION

The present invention relates generally to computing a probe position within a living body, and specifically to computing a probe position in different coordinate frames.

BACKGROUND

Tracking the position of intrabody probes, such as insertion tubes, catheters and implants, is required for many medical procedures. For example, U.S. Patent Application Publication 2014/0095105 describes an algorithm to correct and/or scale an electrical current-based coordinate system that can include the determination of one or more global transformation or interpolation functions and/or one or more local transformation functions. The global and local transformation functions can be determined by calculating a global metric tensor and a number of local metric tensors. The metric tensors can be calculated based on pre-determined and measured distances between closely-spaced sensors on a catheter.

US Patent Publication 2016/0367168 of Malinin, et al., describes computation of a location of a number of fiducial points. The fiducial points can include impedance locations of an electrode disposed on a catheter in an impedance-based coordinate system and magnetic locations of a magnetic position sensor disposed on the catheter in a magnetic based coordinate system. The impedance location of the electrode in the impedance-based coordinate system can be transformed into a transformed impedance location of the electrode in the magnetic based coordinate system. A magnetic location of the electrode in the magnetic based coordinate system can be determined. A determination of whether an impedance shift exists between the transformed impedance location of the electrode in the magnetic based system and the magnetic location of the electrode in the magnetic based system can be made. An electromagnetic dynamic registration can be generated between the impedance-based coordinate system and the magnetic based coordinate system based on the impedance shift.

US Patent Publication 2011/0238083 of Moll, et al., describes an apparatus comprised of a flexible sheath instrument, a flexible guide instrument, and a tool. The flexible sheath instrument comprises a first instrument base removably coupleable to an instrument driver and defines a sheath instrument working lumen. The flexible guide instrument comprises a second instrument base removably coupleable to the instrument driver and is threaded through the sheath instrument working lumen. The guide instrument also defines a guide instrument working lumen. The tool is threaded through the guide instrument working lumen. For this embodiment of the apparatus, the sheath instrument and guide instrument are independently controllable relative to each other.

US Patent Publication 2007/0135803 of Belson describes an apparatus for use in a transluminal procedure. The apparatus, comprising, for example, a housing having a guide lumen and a seal proximal to a distal end of the housing that extends across and completely seals the guide lumen; a fixation element in the housing and adapted to secure the distal end of the housing to tissue; and a channel extending through the side wall of the housing having an outlet in communication with the lumen distal of the seal. Methods are also provided. For example, a method includes, performing a transluminal procedure by: securing a datum and position indicator to a wall of a target lumen; forming an opening in the wall; advancing an instrument through the opening; and tracking the advancement of the instrument using the datum and position indicator.

SUMMARY

There is provided in accordance with an embodiment of the present disclosure a medical probe tracking system, including a plurality of body surface electrodes configured to be applied to a skin surface of a living subject, a first probe configured to be inserted into a body of the living subject and including first probe electrodes, a second probe configured to be inserted into the body of the living subject and including second probe electrodes and a magnetic field sensor, a magnetic field generator configured to generate a magnetic field within the body of the living subject, a display, and processing circuitry configured to measure first and second electrical currents between the body surface electrodes and the first and second probe electrodes within the body, respectively, compute first position coordinates of the first probe in a first coordinate frame responsively to a distribution of the first electrical currents, receive magnetic position signals from the magnetic field sensor in response to the magnetic field, render to the display an initial three-dimensional (3D) representation of the first probe in the first coordinate frame and then compute a current-position map (CPM) between a distribution of the second electrical currents and the magnetic position signals with respect to a second coordinate frame defined by the magnetic field generator, find a transformation between the first and second coordinate frames, apply the transformation to the first position coordinates yielding second position coordinates of the first probe in the second coordinate frame, and render to the display a modified 3D representation of the first probe the second position coordinates in the second coordinate frame.

Further in accordance with an embodiment of the present disclosure the processing circuitry is configured to render the initial 3D representation of the first probe the first coordinate frame prior to computation of the CPM and render the modified 3D representation of the first probe the second coordinate frame after computation of the CPM.

Still further in accordance with an embodiment of the present disclosure the transformation includes a rotation and a translation element, the first position coordinates including a location and an orientation, the second position coordinates having a location and an orientation, the processing circuitry being configured to render the modified 3D representation of the first probe based on the location and the orientation of the second position coordinates.

Additionally, in accordance with an embodiment of the present disclosure the second probe includes a balloon catheter having a shaft, an inflatable balloon fitted at a distal end of the shaft, multiple electrodes of the second probe electrodes disposed on the inflatable balloon, the magnetic field sensor being disposed at a proximal end of the shaft, the processing circuitry being configured to find a balloon rotation matrix from a rotation between a first plane defined by the multiple electrodes and a second plane defined by electrodes in a balloon catheter model, and find the transformation based on balloon rotation matrix.

Moreover, in accordance with an embodiment of the present disclosure the second position coordinates are located externally to a volume in which the CPM provides a mapping.

Further in accordance with an embodiment of the present disclosure the processing circuitry is configured to render the modified 3D representation of the first probe the transformed second position coordinates, and a 3D representation of the second probe based at least on any one or more of the following a magnetic position derived from the CPM, and from the magnetic field detected by the magnetic field sensor.

There is also provided in accordance with still another embodiment of the present disclosure a medical probe tracking system, including a plurality of body surface electrodes configured to be applied to a skin surface of a living subject, a probe configured to be inserted into a body of the living subject and including probe electrodes and a magnetic field sensor, a magnetic field generator configured to generate a magnetic field within the body of the living subject, a display, and processing circuitry configured to measure electrical currents between the body surface electrodes and the probe electrodes within the body, respectively, compute first position coordinates of the probe in a first coordinate frame responsively to a distribution of a first multiplicity of the electrical currents, receive magnetic position signals from the magnetic field sensor in response to the magnetic field, render to the display an initial three-dimensional (3D) representation of the probe in the first coordinate frame and then compute a current-position map (CPM) between a distribution of a second multiplicity of the electrical currents and the magnetic position signals with respect to a second coordinate frame defined by the magnetic field generator, find a transformation between the first and second coordinate frames, apply the transformation to the first position coordinates yielding second position coordinates of the probe in the second coordinate frame, and render to the display a modified 3D representation of the probe the second position coordinates in the second coordinate frame.

Still further in accordance with an embodiment of the present disclosure the processing circuitry is configured to render the initial 3D representation of the probe the first coordinate frame prior to computation of the CPM, and render the modified 3D representation of the probe the second coordinate frame after computation of the CPM.

Additionally, in accordance with an embodiment of the present disclosure the transformation includes a rotation and a translation element, the first position coordinates including a location and an orientation, the second position coordinates having a location and an orientation, the processing circuitry being configured to render the modified 3D representation of the probe based on the location and the orientation of the second position coordinates.

Moreover, in accordance with an embodiment of the present disclosure the probe includes a balloon catheter having a shaft, an inflatable balloon fitted at a distal end of the shaft, multiple electrodes of the probe electrodes disposed on the inflatable balloon, the magnetic field sensor being disposed at a proximal end of the shaft, the processing circuitry being configured to find a balloon rotation matrix from a rotation between a first plane defined by the multiple electrodes and a second plane defined by electrodes in a balloon catheter model, and find the transformation based on balloon rotation matrix.

Further in accordance with an embodiment of the present disclosure the second position coordinates are located externally to a volume in which the CPM provides a mapping.

Still further in accordance with an embodiment of the present disclosure the processing circuitry is configured to render a further modified 3D representation of the probe third position coordinates located in the volume based on at least any one or more of the following a magnetic position derived from the CPM based on a distribution of a third multiplicity of the electrical currents, and from the magnetic field detected by the magnetic field sensor.

There is also provided in accordance with still another embodiment of the present disclosure a medical probe tracking method, including applying a plurality of body surface electrodes to a skin surface of a living subject, inserting including first probe electrodes a first probe into a body of the living subject, inserting a second probe including second probe electrodes and a magnetic field sensor into the body of the living subject, generating, by a magnetic field generator, a magnetic field within the body of the living subject, measuring first and second electrical currents between the body surface electrodes and the first and second probe electrodes within the body, respectively, computing first position coordinates of the first probe in a first coordinate frame responsively to a distribution of the first electrical currents, receiving magnetic position signals from the magnetic field sensor in response to the magnetic field, rendering to the display an initial three-dimensional (3D) representation of the first probe in the first coordinate frame and then computing a current-position map (CPM) between a distribution of the second electrical currents and the magnetic position signals with respect to a second coordinate frame defined by the magnetic field generator, finding a transformation between the first and second coordinate frames, applying the transformation to the first position coordinates yielding second position coordinates of the first probe in the second coordinate frame, and rendering to the display a modified 3D representation of the first probe the second position coordinates in the second coordinate frame.

Additionally, in accordance with an embodiment of the present disclosure the rendering of the initial 3D representation is performed prior to the computing of the CPM and the render of the modified 3D representation is performed after the computing of the CPM.

Moreover, in accordance with an embodiment of the present disclosure the transformation includes a rotation and a translation element, the first position coordinates including a location and an orientation, the second position coordinates having a location and an orientation, the rendering of the modified 3D representation including rendering the modified 3D representation of the first probe based on the location and the orientation of the second position coordinates.

Further in accordance with an embodiment of the present disclosure the second probe includes a balloon catheter having a shaft, an inflatable balloon fitted at a distal end of the shaft, multiple electrodes of the second probe electrodes disposed on the inflatable balloon, the magnetic field sensor being disposed at a proximal end of the shaft, the method further including finding a balloon rotation matrix from a rotation between a first plane defined by the multiple electrodes and a second plane defined by electrodes in a balloon catheter model, and finding the transformation based on balloon rotation matrix.

Still further in accordance with an embodiment of the present disclosure the second position coordinates are located externally to a volume in which the CPM provides a mapping.

Additionally, in accordance with an embodiment of the present disclosure, the method includes rendering the modified 3D representation of the first probe the transformed second position coordinates, and a 3D representation of the second probe based at least on any one or more of the following a magnetic position derived from the CPM, and from the magnetic field detected by the magnetic field sensor.

There is also provided in accordance with still another embodiment of the present disclosure a medical probe tracking method, including applying a plurality of body surface electrodes to a skin surface of a living subject, inserting a probe including probe electrodes and a magnetic field sensor into a body of the living subject, generating, by a magnetic field generator, a magnetic field within the body of the living subject, measuring electrical currents between the body surface electrodes and the probe electrodes within the body, respectively, computing first position coordinates of the probe in a first coordinate frame responsively to a distribution of a first multiplicity of the electrical currents, receiving magnetic position signals from the magnetic field sensor in response to the magnetic field, rendering to the display an initial three-dimensional (3D) representation of the probe in the first coordinate frame and then compute a current-position map (CPM) between a distribution of a second multiplicity of the electrical currents and the magnetic position signals with respect to a second coordinate frame defined by the magnetic field generator, finding a transformation between the first and second coordinate frames, applying the transformation to the first position coordinates yielding second position coordinates of the probe in the second coordinate frame, and rendering to the display a modified 3D representation of the probe the second position coordinates in the second coordinate frame.

Moreover, in accordance with an embodiment of the present disclosure the rendering of the initial 3D representation is performed prior to the computing of the CPM and the render of the modified 3D representation is performed after the computing of the CPM.

Further in accordance with an embodiment of the present disclosure the transformation includes a rotation and a translation element, the first position coordinates including a location and an orientation, the second position coordinates having a location and an orientation, the rendering of the modified 3D representation including rendering the modified 3D representation of the first probe based on the location and the orientation of the second position coordinates.

Still further in accordance with an embodiment of the present disclosure the probe includes a balloon catheter having a shaft, an inflatable balloon fitted at a distal end of the shaft, multiple electrodes of the probe electrodes disposed on the inflatable balloon, the magnetic field sensor being disposed at a proximal end of the shaft, the method further including finding a balloon rotation matrix from a rotation between a first plane defined by the multiple electrodes and a second plane defined by electrodes in a balloon catheter model, and finding the transformation based on balloon rotation matrix.

Additionally, in accordance with an embodiment of the present disclosure the second position coordinates are located externally to a volume in which the CPM provides a mapping.

Moreover, in accordance with an embodiment of the present disclosure, the method includes rendering a further modified 3D representation of the probe third position coordinates located in the volume based on at least any one or more of the following a magnetic position derived from the CPM based on a distribution of a third multiplicity of the electrical currents, and from the magnetic field detected by the magnetic field sensor.

BRIEF DESCRIPTION OF THE DRAWINGS

The present invention will be understood from the following detailed description, taken in conjunction with the drawings in which:

FIG. 6 is a view of a flowchart including exemplary steps in a magnetic-based position tracking method for use in the system of FIG. 1;

FIG. 7 is a view of a flowchart including exemplary steps in a hybrid magnetic-current-distribution-based position tracking method for use in the system of FIG. 1;

DESCRIPTION OF EXAMPLE EMBODIMENTS

Overview

Figure 1:
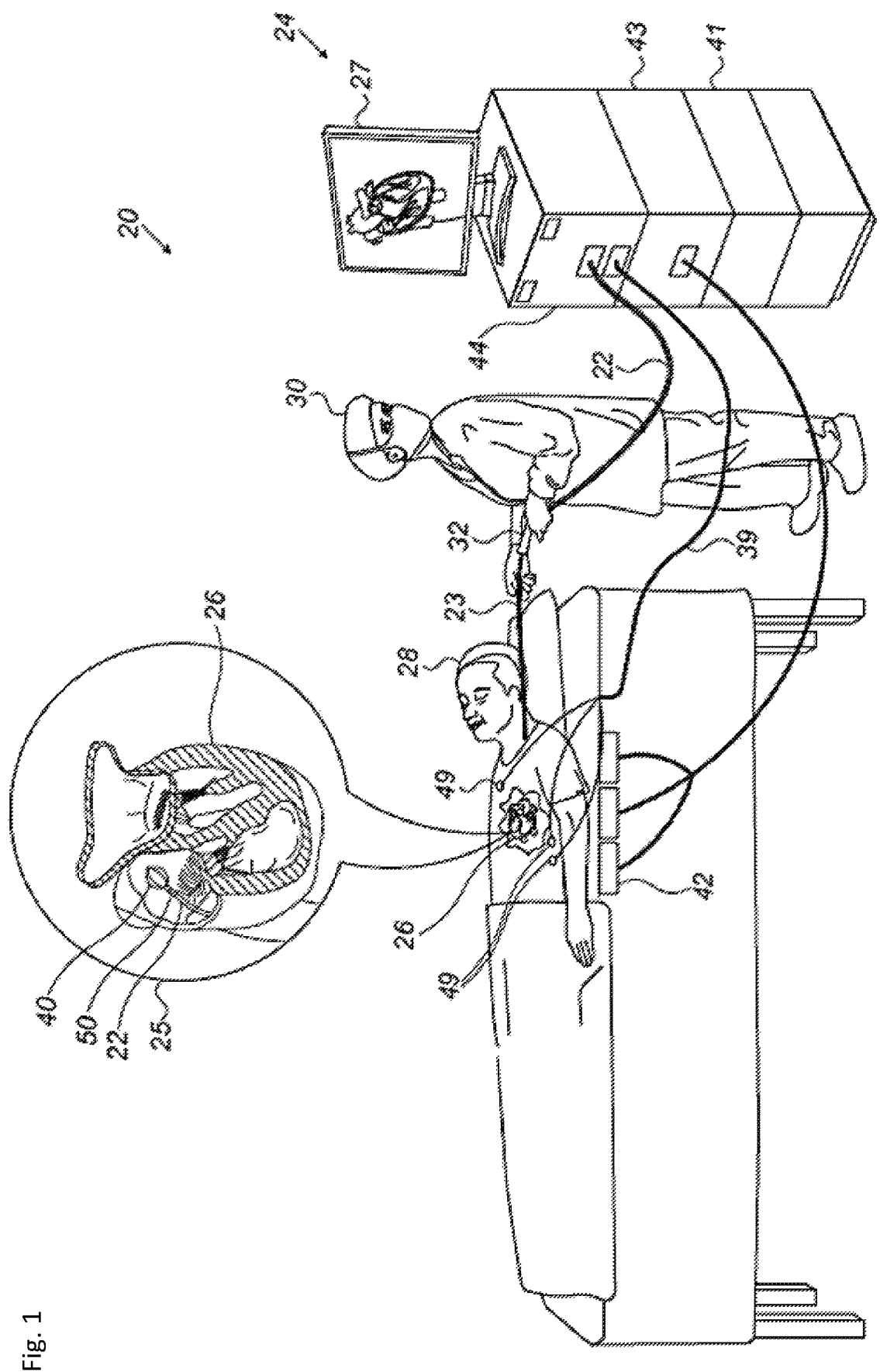
FIG. 1 is a schematic pictorial illustration of a catheter-based position tracking system in accordance with an embodiment of the present invention.

The Carto®3 system applies Active Current Location (ACL) hybrid position-tracking technology. In ACL technology, distribution of measured currents associated with the probe electrodes are correlated with a current-to-position matrix (CPM), which maps the current distribution with a position that was previously acquired from magnetic location-calibrated position signals. The ACL technology enables locating and visualizing a catheter (even a catheter which does not have a magnetic field sensor), but only in the volume(s) where the CPM has been computed, by a catheter with a magnetic sensor. A prerequisite for building the CPM, is to insert a magnetic-field sensor-equipped catheter into a body and move the catheter in a volume of the body, in order to compute the CPM for that volume.

Catheters outside of the CPM volume are not trackable or visualized when using ACL. For example, a Coronary Sinus catheter may sometimes not be visualized because it is located outside the CPM volume. A balloon catheter with a proximal magnetic field sensor can also have difficulty being visualized due to the distance of the magnetic field sensor from the electrodes disposed on the inflatable balloon of the catheter. A Lasso® guidewire catheter, used in conjunction with a balloon catheter which enters a heart chamber before any other magnetic-field sensor-equipped catheter is present in the chamber, will also not be visualized using ACL. The fact that ACL cannot be used outside of the CPM volume might complicate some clinical workflows, such as a PVI (Pulmonary Vein Isolation) workflow with a balloon catheter and a Lasso® guidewire catheter, which does not have a magnetic-field sensor.

Independent Current Location (ICL) technology may be used to visualize catheters which do not include a magnetic field sensor. ICL is based on locating catheters according to current distribution between catheter electrodes and body surface patches. ICL does not require a magnetic-field sensor-equipped catheter for enabling catheter visualization. ICL technology can visualize a catheter without the need to pre-acquire a CPM by a magnetic-field sensor-equipped catheter. ICL technology enables, for example, visualization of the Lasso® guidewire catheter immediately after the Lasso® guidewire catheter exits its sheath, without the need to pre-acquire the CPM by another catheter. ICL also enables visualization of the balloon catheter electrodes. In ICL, a local scaling factor may be applied for each voxel or cell of a volume in the body where the catheter needs to be visualized. The factor may be determined using a catheter with multiple electrodes having a known spatial relationship, such as a Lasso-shaped catheter. The scaling factors are used to improve the accuracy of pure current distribution-based locations.

The limitation of ICL technology is its accuracy even after applying scaling factors. It is less accurate than magnetic tracking or ACL. Additionally, the coordinate frame used by ICL is different from the coordinate frame used by ACL and the two coordinate frames are not aligned in displacement, rotation and in scaling. Due to the above limitations, ICL-based visualization and mapping cannot be successfully superimposed with ACL-based visualization and mapping.

In embodiments of the present invention, ICL and ACL are selectively combined providing advantages of both ICL and ACL. ICL tracking technology is used prior to CPM computation in order to track both non-magnetic-field sensor-equipped catheters and magnetic-field sensor-equipped catheters. The catheters may be initially visualized based on the ICL coordinate frame.

After the CPM has been computed based on measurement from a magnetic-field sensor-equipped catheter, a local transformation between the ICL coordinate frame and the ACL coordinate frame is found. The transformation may then be applied to positions in the ICL coordinate frame, including the positions that were computed prior to the CPM being computed. The transformed positions may then be used to visualize the catheters in the ACL coordinate frame.

Additionally, after the CPM has been computed, ICL may continue to be used for probes located externally to the volume of the CPM. For probes located inside the CPM volume, ACL or ICL may be used. The computed positions in the ICL coordinate frame may then be transformed to the ACL coordinate frame. 3D representations of probes may then be rendered to a display showing the position of the probes according to the ACL coordinate frame based on ACL positions which were transformed from the ICL coordinate frame and/or ACL positions derived from the CPM and/or magnetic field-based tracking.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 2:
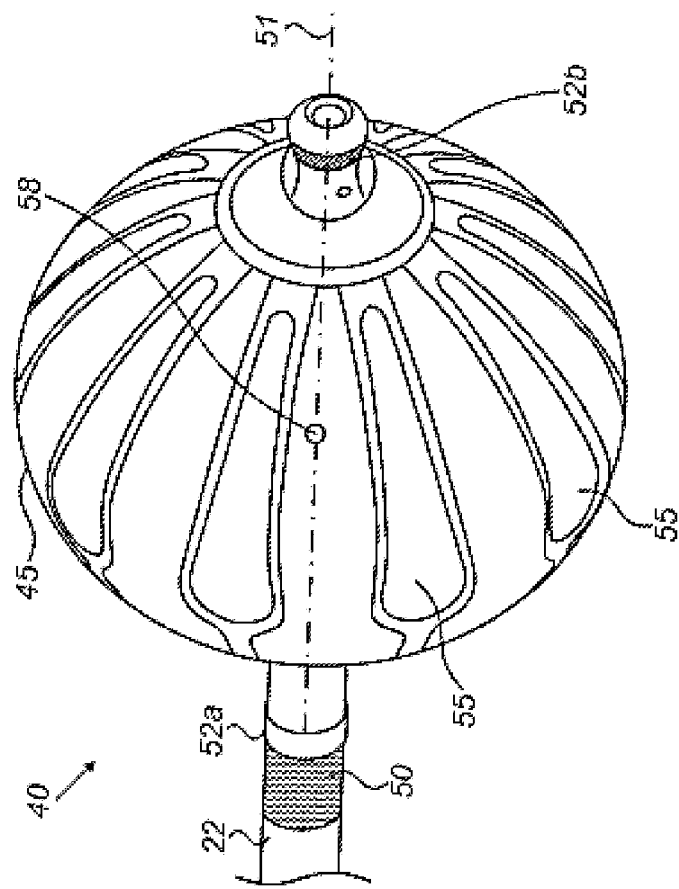
FIG. 2 is a schematic pictorial illustration of a balloon catheter used in the system of FIG. 1.

Reference is now made to FIG. 1, which is a schematic pictorial illustration of a catheter-based position tracking system 20 in accordance with an embodiment of the present invention. Reference is also made to FIG. 2, which is a schematic pictorial illustration of a balloon catheter 40, in accordance with an embodiment of the present invention. A balloon catheter has been used by way of example. Any suitable catheter or probe may be used in conjunction with the system 20 whether the catheter or probe is used for ablation or for another purpose.

The position tracking system 20 is used to determine the position of the balloon catheter 40, seen in an inset 25 of FIG. 1 and in more detail in FIG. 2. The balloon catheter 40 includes a shaft 22 and an inflatable balloon 45 fitted at a distal end of the shaft 22. Typically, the balloon catheter 40 is used for therapeutic treatment, such as spatially ablating cardiac tissue, for example at the left atrium.

The position tracking system 20 can determine a position and orientation of the shaft 22 of the balloon catheter 40 based on sensing-electrodes 52 (proximal-electrode 52$a$ and distal-electrode 52$b$) fitted on the shaft 22, on either side of the inflatable balloon 45 and a magnetic sensor 50 fitted just proximally to proximal-electrode 52$a$, and optionally ablation electrodes 55 describe in more detail below. The proximal-electrode 52$a$, the distal-electrode 52$b$, and the magnetic sensor 50 are connected by wires running through the shaft 22 to various driver circuitries in a console 24. In some embodiments, the distal-electrode 52$b$ may be omitted.

The shaft 22 defines a longitudinal axis 51. A center point 58 on the axis 51, which is the origin of the sphere shape of the inflatable balloon 45, defines a nominal position of the inflatable balloon 45. The ablation electrodes 55 are disposed in a circumference over the inflatable balloon 45, which occupy a large area as compared with sensing-electrodes 52$a$ and 52$b$. Radio frequency power may be supplied to the ablation electrodes 55 to ablate the cardiac tissue.

Typically, the disposed ablation electrodes 55 are evenly distributed along an equator of the inflatable balloon 45, where the equator is generally aligned perpendicular to the longitudinal axis 51 of the distal end of the shaft 22.

The illustration shown in FIG. 2 is chosen purely for the sake of conceptual clarity. Other configurations of sensing-electrodes 52 and ablation electrodes 55 are possible. Additional functionalities may be included in the magnetic sensor 50. Elements which are not relevant to the disclosed embodiments of the invention, such as irrigation ports, are omitted for the sake of clarity.

A physician 30 navigates the balloon catheter 40 to a target location in a heart 26 of a patient 28 by manipulating the shaft 22 using a manipulator 32 near the proximal end of the catheter 40 and/or deflection from a sheath 23. The balloon catheter 40 is inserted, while the inflatable balloon 45 is deflated, through the sheath 23, and only after the balloon catheter 40 is retracted from the sheath 23 is the inflatable balloon 45 inflated and regains its intended functional shape. By containing balloon catheter 40 in a deflated configuration, the sheath 23 also serves to minimize vascular trauma on its way to the target location.

Console 24 comprises processing circuitry 41, typically a general-purpose computer and a suitable front end and interface circuits 44 for generating signals in, and/or receiving signals from, body surface electrodes 49 which are attached by wires running through a cable 39 to the chest and to the back of the patient 28. The body surface electrodes 49 are configured to be applied to a skin surface of a living subject (e.g., the patient 28).

Console 24 further comprises a magnetic-sensing subsystem. The patient 28 is placed in a magnetic field generated by a pad containing magnetic field generator coils 42, which are driven by a unit 43 disposed in the console 24. The magnetic fields generated by the coils 42 generate directional signals in the magnetic sensor 50, which are then provided as corresponding electrical inputs to the processing circuitry 41.

In some embodiments, the processing circuitry 41 uses position-signals received from the sensing-electrodes 52, the magnetic sensor 50 and the ablation electrodes 55 to estimate a position of the balloon catheter 40 inside an organ, such as inside a cardiac chamber. In some embodiments, the processing circuitry 41 correlates the position signals received from the electrodes 52, 55 with previously acquired magnetic location-calibrated position signals, to estimate the position of the balloon catheter 40 inside a cardiac chamber. The position coordinates of the sensing-electrodes 52 and the ablation electrodes 55 may be determined by the processing circuitry 41 based on, among other inputs, measured impedances, voltages or on proportions of currents distribution, between the electrodes 52, 55 and the surface electrodes 49. The console 24 drives a display 27, which shows the distal end of the catheter position inside the heart 26.

The method of position sensing using current distribution measurements and/or external magnetic fields is implemented in various medical applications, for example, in the Carto® system, produced by Biosense Webster Inc. (Irvine, Calif.), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publications 2002/0065455 A1, 2003/0120150 A1 and 2004/0068178 A1, whose disclosures are all incorporated herein by reference.

The Carto®3 system applies Active Current Location (ACL) which is a hybrid current-distribution and magnetic-based position-tracking technology. In some embodiments, using ACL, the processing circuitry 41 estimates the positions of the sensing-electrodes 52 and the ablation electrodes 55. In some embodiments, the signals received from the electrodes 52, 55 are correlated with a current-to-position matrix (CPM) which maps current distribution ratios (or another electrical value) with a position that was previously acquired from magnetic location-calibrated position signals. The current distribution ratios are based on measurements of the body surface electrodes 49 of current flowing from the electrodes 52, 55 to the body surface electrodes 49.

In some embodiments, to visualize catheters which do not include a magnetic sensor, the processing circuitry 41 may apply an electrical signal-based method, referred to as Independent Current Location (ICL) technology. In ICL, the processing circuitry 41 calculates a local scaling factor for each voxel of the volume in which catheters are visualized. The factor is determined using a catheter with multiple electrodes having a known spatial relationship, such as a lasso-shaped catheter. However, although yielding accurate local scaling (e.g., over several millimeters), ICL is less accurate when applied to a volume of a whole heart chamber, whose size is in the order of centimeters. The ICL method, in which positions are calculated based on current distribution proportions can have errors and may yield a distorted shape of the balloon catheter 40, due to the non-linear nature of the current-based ICL space. In some embodiments, the processing circuitry 41 may apply the disclosed ICL method to scale ICL space and the balloon catheter shape into a correct one, based on known smaller scale distances between electrodes of a lasso-shaped catheter, as well as based on larger scale distances, themselves based on the known distance between the sensing-electrodes 52 at the ends of the inflatable balloon 45.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

FIG. 1 shows only elements related to the disclosed techniques, for the sake of simplicity and clarity. The system 20 typically comprises additional modules and elements that are not directly related to the disclosed techniques, and thus are intentionally omitted from FIG. 1 and from the corresponding description.

Figure 3:
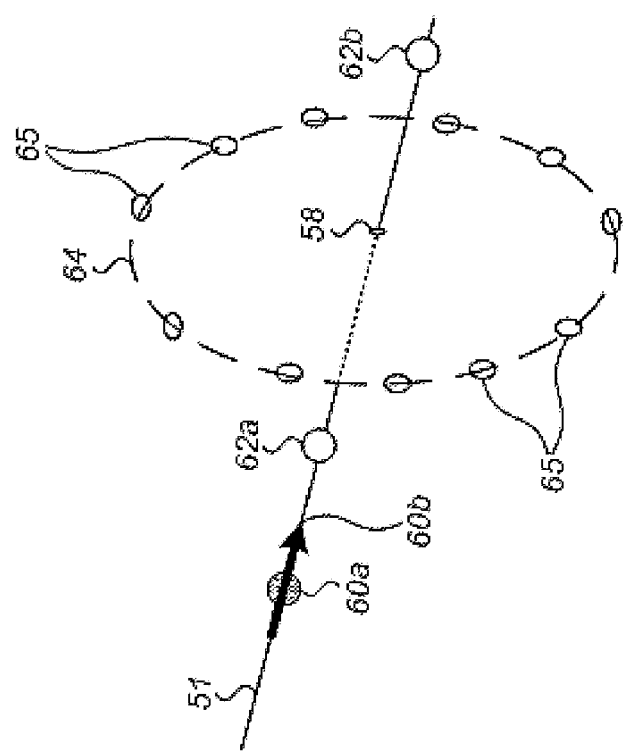
FIG. 3 is a schematic pictorial illustration of various datum points over the balloon catheter of FIG. 2.

Reference is now made to FIG. 3, which is a schematic pictorial illustration of various datum points over the balloon catheter 40 of FIG. 2, in accordance with an embodiment of the present invention. Reference is also made to FIG. 2. The location of the datum points may be presented, for example, in a coordinate frame defined for the electro-anatomical map stored in the processing circuitry 41, to which the system 20 correlates the position in space of the balloon 40.

FIG. 3 shows that the proximal-electrode 52a is located at a position 62a, while distal electrode 52b is located at a position 62b. The magnetic sensor 50 is located at a position 60a, while, as described above, the sensor 50 is capable of indicating a direction 60b, which is parallel to the direction of shaft 22 (i.e., parallel to the axis 51). Despite the large areas of ablation electrodes 55, a consistent and useful general representation of the electrodes 55 in space is possible, in the form of electrode positions 65 on a circle 64 (forming an equator of the inflatable balloon 45) embedded in a plane orthogonal to the axis 51. In other words, when the balloon is fully inflated, the electrode positions 65 should ideally lay on the circle 64 which has the maximal transverse diameter of the inflatable balloon 45 (FIG. 2). A nominal position of the inflatable balloon 45 is ideally defined by center point 58, which is also the center of the circler 64. Assuming, the electrode positions 65 provide accurate and meaningful data of the position of the ablation electrodes 55, the electrode positions 65 and the circle 64 that they define may be used to compute the position and orientation of the inflatable balloon 45. The electrode positions may be computed based on ACL technology or by using ICL technology. As mentioned above, the coordinate frames of ACL and ICL are different and therefore, to use ICL positions with ACL or magnetic based positions (such as position 60a), the ICL positions are first transformed to ACL coordinate space described in detail with reference to FIGS. 9-12 below.

The ICL, magnetic and ACL tracking technologies are now described below in more detail with reference to FIGS. 4-8.

Figure 4:
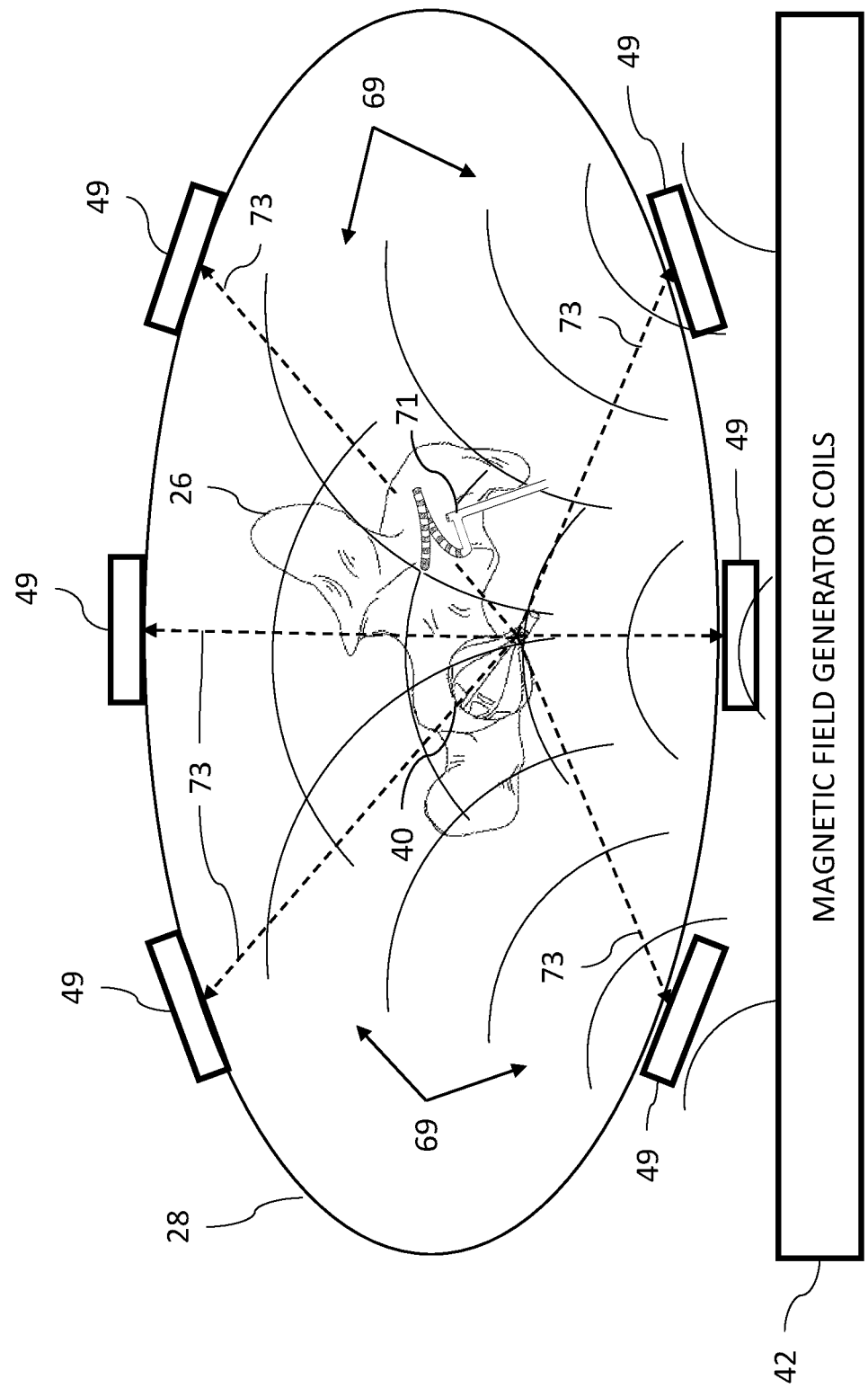
FIG. 4 is a schematic partly-pictorial, partly block-diagram view illustrating position tracking in the system of FIG. 1.

Reference is now made to FIG. 4, which is a schematic partly-pictorial, partly block-diagram view illustrating position tracking in the system 20 of FIG. 1. The surface electrodes 49 are applied to the chest and back of the patient 28. The magnetic field generator coils 42 form a magnetic field generator, and are disposed below the patient 28 and generate a magnetic field 69 within the body of the patient 28. FIG. 4 shows two catheters in a chamber of the heart 26, the balloon catheter 40 and a lasso-shaped catheter 71. The balloon catheter 40 includes the magnetic sensor 50 whereas the lasso-shaped catheter 71 does not include a magnetic field sensor. FIG. 4 also shows lines 73 representative of electric current flow between the proximal-electrode 52a (FIG. 2) of the balloon catheter 40 and the surface electrodes 49.

Figure 5:
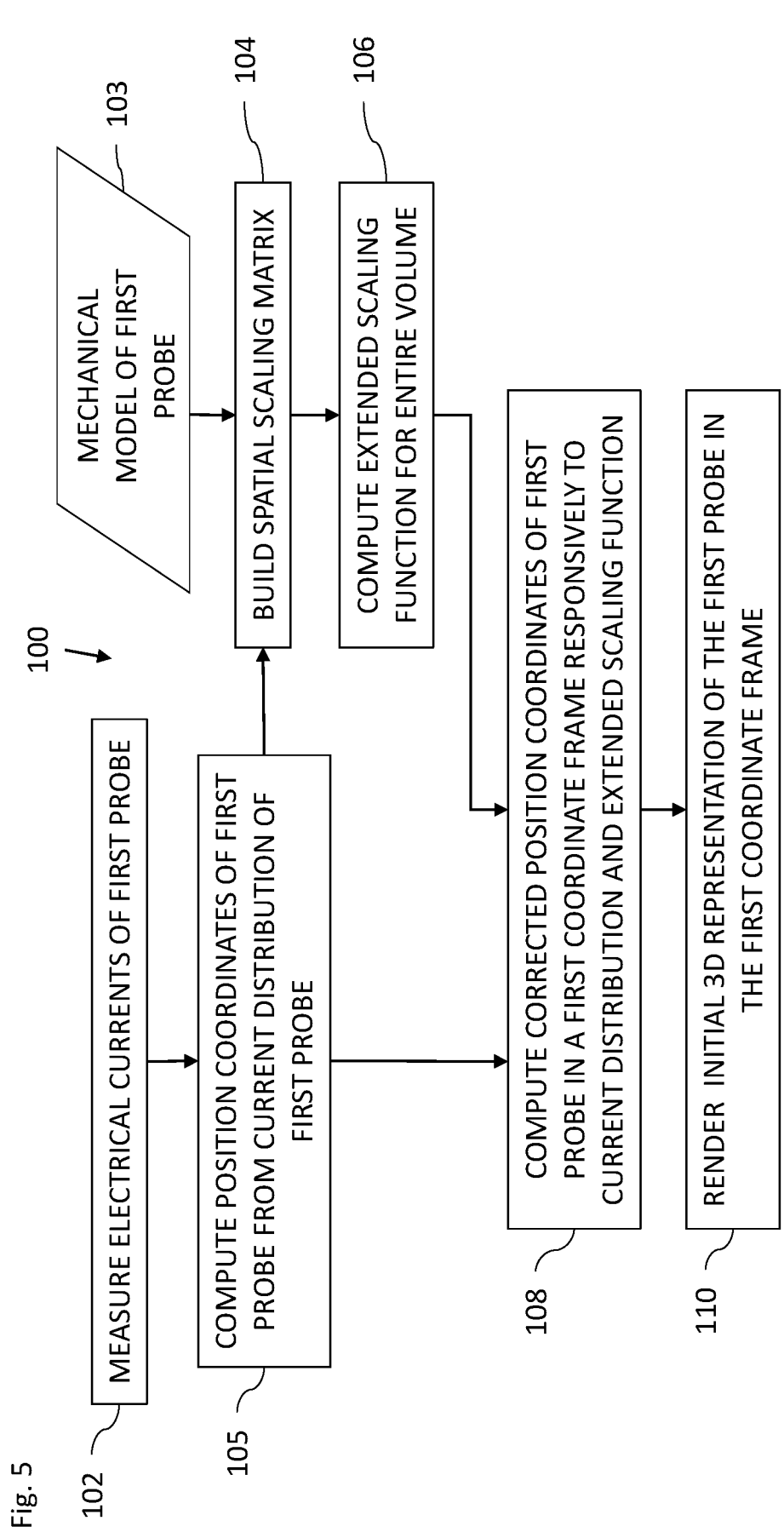
FIG. 5 is a view of a flowchart including exemplary steps in a current-distribution-based position tracking method for use in the system of FIG. 1.

Reference is now made to FIG. 5, which is a view of a flowchart 100 including exemplary steps in a current distribution-based position tracking method, for example, using ICL, for use in the system 20 of FIG. 1. Reference is also made to FIG. 4. The tracking method of FIG. 5 is described with reference to a first probe configured to be inserted into a body of a living subject. The first probe may be an ablation catheter, for example, the balloon catheter 40, or a non-ablation catheter or probe, for example, the lasso-shaped catheter 71. Additionally, the first probe may be used in the heart or any other body part of a body of a living subject. The first probe includes first probe electrodes, e.g. the sensing-electrodes of the lasso-shaped catheter 71. In accordance with one embodiment, the first probe does not include a magnetic field sensor. In accordance with another embodiment, the first probe includes a magnetic field sensor, e.g., the magnetic sensor 50.

The processing circuitry 41 (FIG. 1) is configured to measure (block 102) electrical currents between the first probe electrodes within the body and the body surface electrodes 49. The processing circuitry 41 is configured to compute (block 105) initial position coordinates of the first probe from current distributions of the first probe. The processing circuitry 41 is also configured to generate (block 104) local scaling cells and combine the local scaling cells to build a spatial scaling matrix, for example, based on a mechanical model 103 of the first probe, e.g., based on a known spacing between the first probe electrodes (e.g., the sensing-electrodes of the lasso-shaped catheter 71) and compute (block 106) an extended scaling function for an entire volume by extrapolating from the local scaling cells of the spatial scaling matrix, for the entire volume.

The processing circuitry 41 is configured to compute (block 108) first (corrected) position coordinates of the first probe in a first coordinate frame (e.g., ICL coordinate frame) responsively to a distribution of the measured electrical currents. The processing circuitry 41 is configured to render (block 110) to the display 27 an initial three-dimensional (3D) representation of the first probe in the first coordinate frame.

In some embodiments, the processing circuitry 41 is configured to render the initial 3D representation of the first probe according to the first coordinate frame prior to computation of a CPM and to render a modified 3D representation of the first probe according to a second coordinate frame (e.g., ACL coordinate frame) after computation of the CPM as described in more detail with reference to FIG. 9. An advantage of using ICL is that rendering in the first coordinate frame (e.g., ICL coordinate frame) is not restricted to the CPM volume.

Reference is now made to FIG. 6, which is a view of a flowchart 120 including exemplary steps in a magnetic-based position tracking method for use in the system 20 of FIG. 1. Reference is also made to FIG. 4. The tracking method of FIG. 6 is described with reference to a second probe configured to be inserted into the body of the living subject. The second probe may be an ablation catheter, for example, the balloon catheter 40, or a non-ablation catheter or probe, for example, the lasso-shaped catheter 71. Additionally, the second probe may be used in the heart or any other body part of a body of a living subject. The second probe includes second probe electrodes, e.g. the sensing-electrodes 52 and/or the ablation electrodes 55. The second probe includes a magnetic field sensor, e.g., the magnetic sensor 50.

In some embodiments, the first probe and the second probe are two different probes, even though the two probes may be the same type of probe subject to space limitations in the body part. In some embodiments, two probes may interact with each other in the body part, e.g., the first probe may pass through the inner lumen of the second probe. In other embodiments, the first probe and the second probe are the same single probe.

The processing circuitry 41 (FIG. 1) is configured to measure (block 122) electrical currents between the second probe electrodes within the body and the body surface electrodes 49. The processing circuitry 41 is configured to receive (block 124) magnetic position signals from a magnetic field sensor (e.g., the magnetic sensor 50) of the second probe in response to the magnetic field 69. The processing circuitry 41 is configured to compute (block 126) magnetic position coordinates of the second probe responsively to the magnetic position signals. The processing circuitry 41 is configured to compute (block 128) a current-position map (or matrix) (CPM) between a distribution of the measured electrical currents (of the step of block 122) and the magnetic position signals with respect to a second coordinate frame (e.g., the magnetic position coordinates) defined by the magnetic field generator. As the second probe is moved, a volume in which the CPM provides a mapping may be expanded by repeating (lines 130) the steps of the blocks 122-128.

Reference is now made to FIG. 7, which is a view of a flowchart 140 including exemplary steps in a hybrid magnetic-current-distribution-based position tracking method, for example, using ACL, for use in the system 20 of FIG. 1. Reference is also made to FIG. 4. The tracking method of FIG. 7 is described with reference to a third probe configured to be inserted into the body of the living subject. The third probe may be the first probe, the second probe or another probe. The third probe may be an ablation catheter, for example, the balloon catheter 40, or a non-ablation catheter or probe, for example, the Lasso-shaped catheter 71. Additionally, the third probe may be used in the heart or any other body part of a body of a living subject. The third probe may include a magnetic field sensor, e.g., the magnetic sensor 50. In some embodiments, the third probe does not include a magnetic field sensor.

The processing circuitry 41 (FIG. 1) is configured to measure (block 142) electrical currents between third probe electrodes of the third probe and the body surface electrodes 49. The processing circuitry 41 is configured to apply (block 144) the CPM to a distribution of the measured electrical currents (measured in the step of block 142) to compute magnetic position coordinates for the third probe based on the distribution of the measured electrical currents of the third probe. The processing circuitry 41 may be configured to render (block 146) a 3D representation of the third probe in the coordinate frame of the computed magnetic position coordinates, i.e., in the second coordinate frame which is also the ACL coordinate frame. If the third probe includes the magnetic sensor 50 or another magnetic field sensor, the 3D representation of the third probe may be rendered based on the magnetic position of the magnetic field sensor and/or the magnetic position coordinates computed from applying the CPM to the distribution of the measured electrical currents. It should be noted that use of the CPM and therefore computing position coordinates from the CPM is generally restricted to the volume in which the CPM has been computed as illustrated in FIG. 8.

Figure 8:
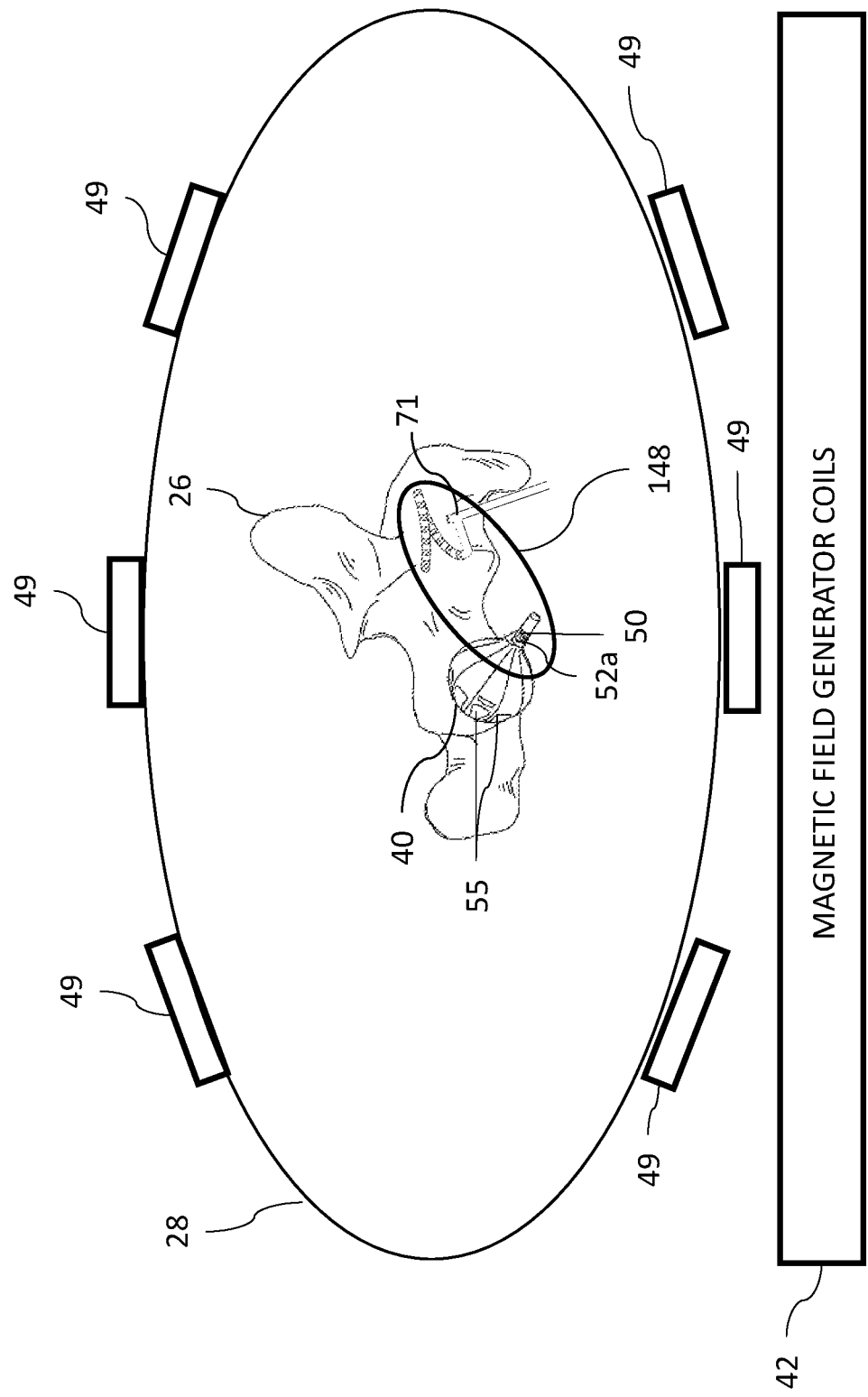
FIG. 8 is a schematic partly-pictorial, partly block-diagram view illustrating a current-position matrix volume in the system of FIG. 1.

Reference is now made to FIG. 8, which is a schematic partly-pictorial, partly block-diagram view illustrating a CPM volume 148 in the system 20 of FIG. 1. FIG. 8 illustrates that although the balloon catheter 40 is providing data for computation of the CPM based on signals from the sensing-electrode 52*a* and the magnetic sensor 50, the ablation electrodes 55 are external to the CPM volume 148. Therefore, the location of the ablation electrodes 55 cannot be determined using ACL. However, the location of the ablation electrodes 55 may be determined using ICL in the first coordinate frame. FIG. 8 also shows that the electrodes of the lasso-shaped catheter 71 are within the CPM volume 148 and therefore the position of the lasso-shaped catheter 71 may be computed using ACL in the second coordinate frame. In the above scenario, the balloon catheter 40 and the lasso-shaped catheter 71 are not rendered together in the same image as the position of the catheters is known in different coordinate frames.

Figure 9:
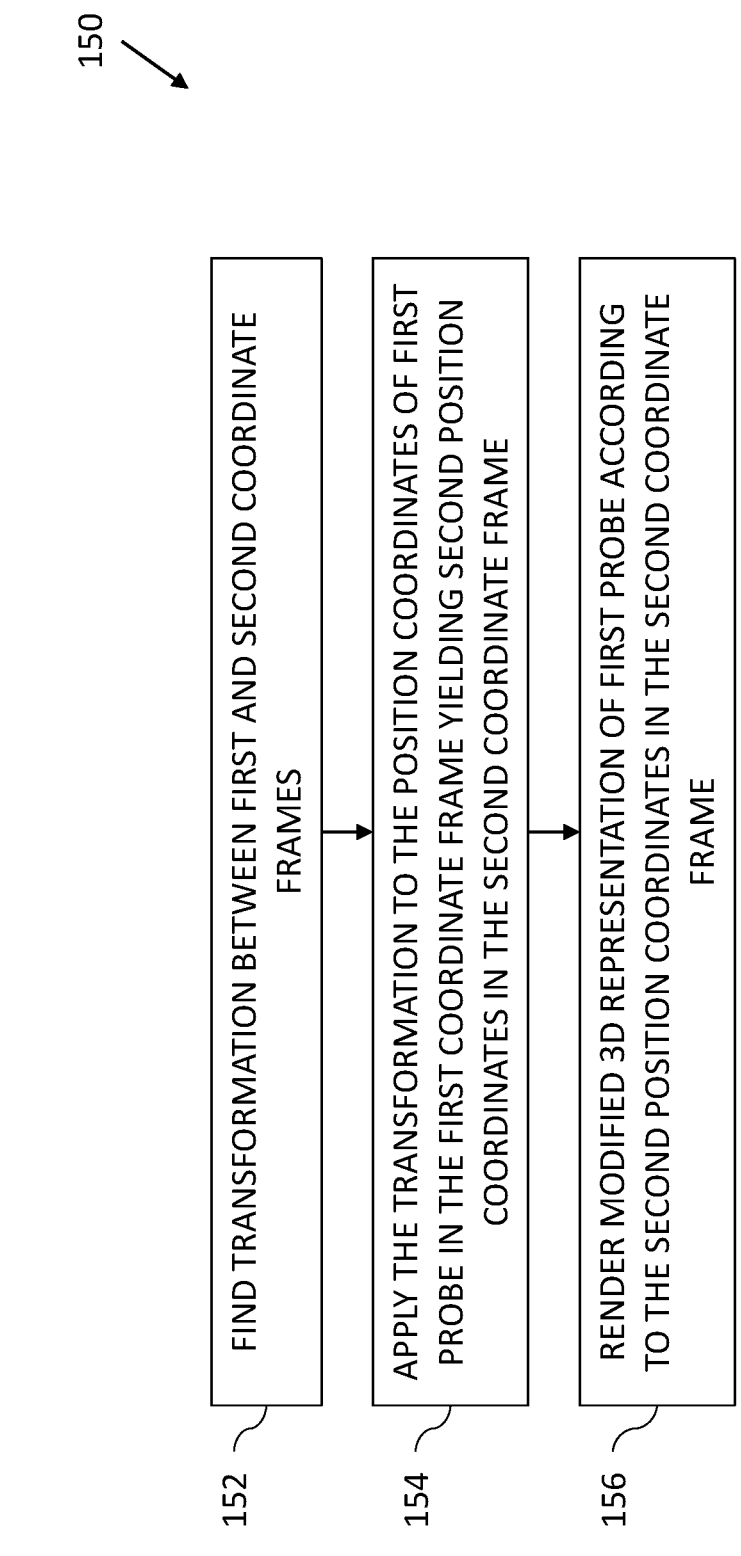
FIG. 9 is a view of a flowchart including exemplary steps in a coordinate frame transformation method for use in the system of FIG. 1.

Reference is now made to FIG. 9, which is a view of a flowchart 150 including exemplary steps in a coordinate frame transformation method for use in the system 20 of FIG. 1. The processing circuitry 41 (FIG. 1) is configured to find (block 152) a transformation between the first and second coordinate frames (i.e., between ICL and ACL coordinate frames). The transformation may be based on using ICL and ACL coordinates measured by the same probe at one or more positions inside the CPM volume 148. The transformation generally includes a rotation and a translation element. An exemplary method for finding the transformation based on the balloon catheter 40 is described in more detail with reference to FIGS. 11 and 12.

The processing circuitry 41 is configured to apply (block 154) the transformation to the first position coordinates of the first probe in the first coordinate frame (i.e., ICL coordinate frame) yielding second position coordinates of the first probe in the second coordinate frame (i.e., ACL coordinate frame). The first position coordinates may include a location and an orientation of the first probe in the first coordinate frame. The second position coordinates may include a location and an orientation of the first probe in the second coordinate frame. The second position coordinates may be located externally to the CPM volume 148 in which the CPM provides a mapping even though using ACL is only possible within the CPM volume 148 without using the transformation from ICL position coordinates.

The processing circuitry 41 is configured to render (block 156) to the display 27 a modified 3D representation of the first probe according to the second position coordinates (e.g., location and orientation) in the second coordinate frame (i.e., ACL coordinate frame). In some embodiments, the rendering step of block 156 is performed after computation of the CPM even though the first position coordinates (which have now been transformed from the ICL to ACL coordinate frame) of the first probe in the first coordinate frame (i.e., ICL coordinate frame) may have been computed prior to the CPM computation.

In some embodiments, the processing circuitry may be configured to render a further modified 3D representation of the first probe according to additional position coordinates which may be ACL coordinates transformed from ICL coordinates computed after computation of the CPM, or according to position coordinates located in the CPM volume 148 based on a magnetic position derived from the CPM based on a distribution of electrical currents using ACL and/or a magnetic position derived from the magnetic field detected by the magnetic field sensor of the first probe.

The first probe may be rendered using any suitable image rendering technique. By way of example, the balloon catheter 40 may be rendered using a graphic processing unit (GPU), based on any suitable method for example, but not limited to, using an imaging method described in US Patent Publication 2018/0182157 of Zar, et al which is herein incorporated by reference. In particular, paragraphs 31 to 48 of the Zar, et al. reference describe rendering quadrics over electroanatomical maps. Examples of quadric surfaces include spheres, ellipsoids, cylinders, cones, hyperbolic paraboloids, paraboloids, and hyperboloids. The imaging may include using mechanical data of splines of the inflatable balloon 45 (FIG. 2), may assume that there is material between the splines of the inflatable balloon 45 and combine various quadrics to form an image of the balloon catheter 40.

Figure 10:
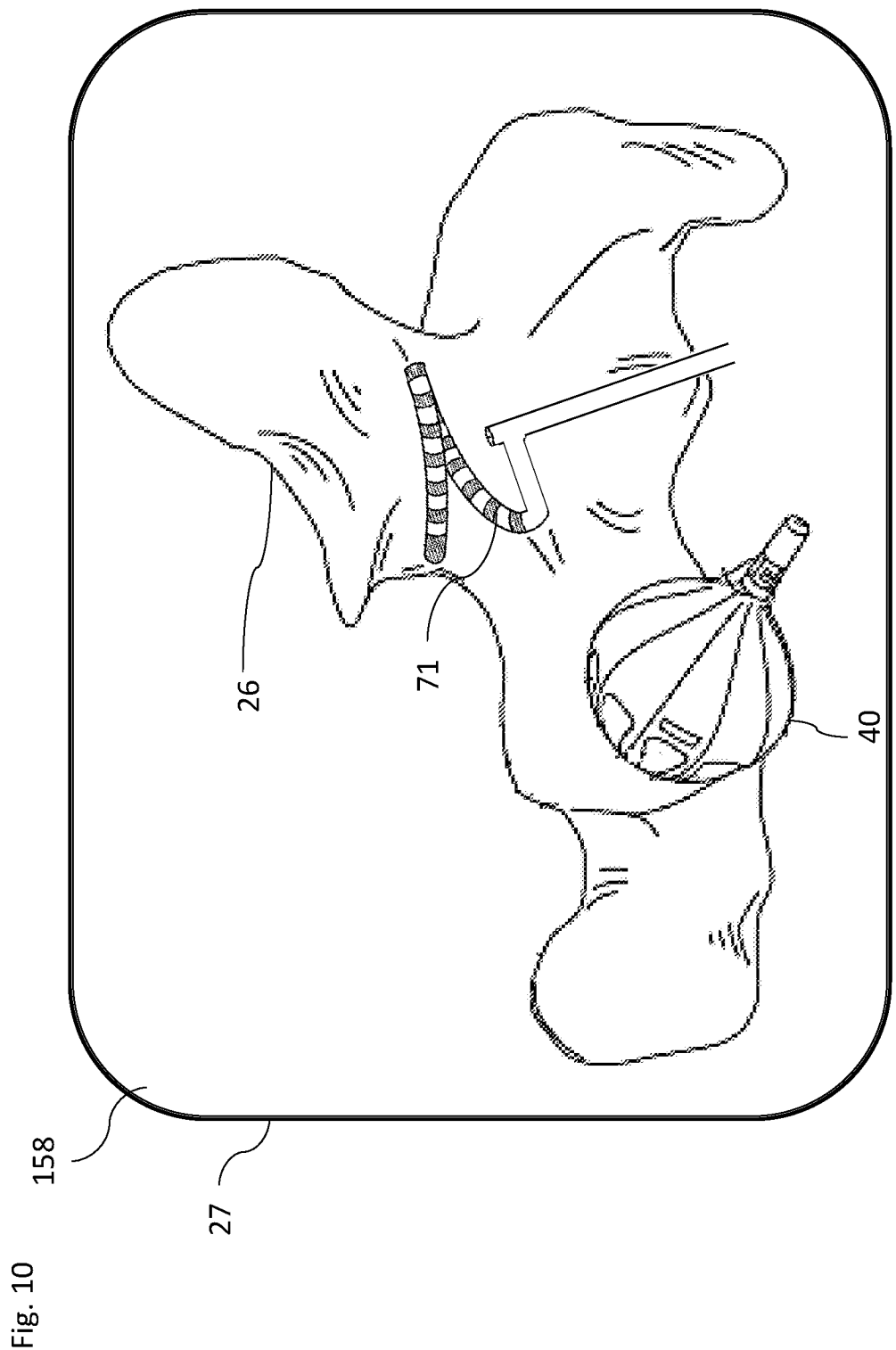
FIG. 10 is a schematic view of a user interface screen showing rendering in the second coordinate frame for use in the system of FIG. 1.

Reference is now made to FIG. 10, which is a schematic view of a user interface screen 158 showing rendering in the second coordinate frame for use in the system 20 of FIG. 1. In some embodiments, the processing circuitry 41 (FIG. 1) is configured to render the user interface screen 158 to the display 27 including the modified 3D representation of the first probe rendered according to the transformed second position coordinates and a 3D representation of the second probe rendered according to a magnetic position derived from the CPM using ACL and/or a magnetic position derived from the magnetic field detected by the magnetic field sensor of the second probe, and/or from coordinates transformed from ICL to ACL using the step of block 154 of FIG. 9. The image rendered to the display is therefore a merged hybrid ICL-ACL-based visualization and mapping. FIG. 10 shows the Lasso-shaped catheter 71 and the balloon catheter 40 being rendered with a 3D representation of the heart 26 in the user interface screen 158 according to the above position tracking methods.

Figure 11:
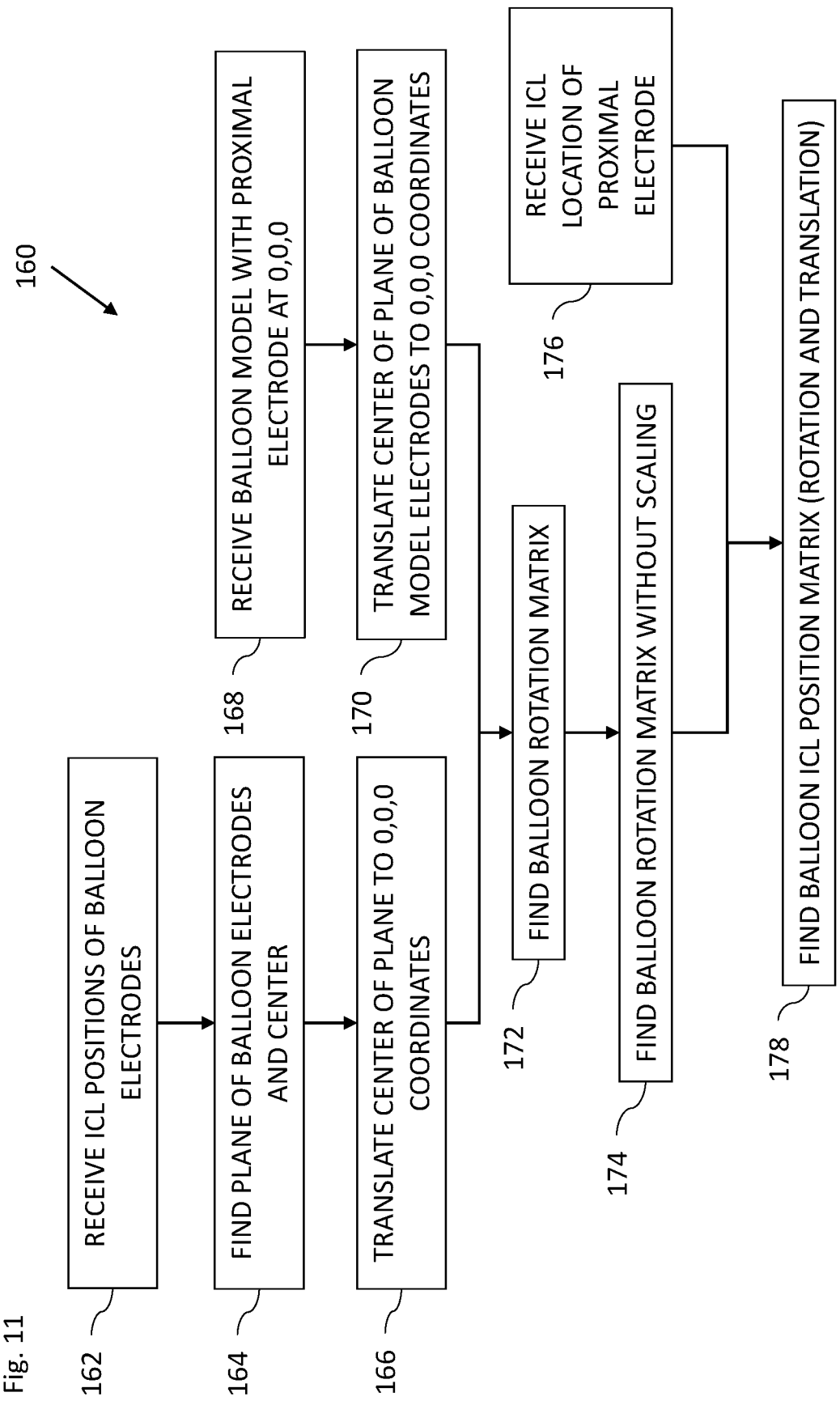
FIG. 11 is a view of a flowchart including exemplary steps in a method to compute a balloon position matrix in the first coordinate frame for use in the system of FIG. 1.

Reference is now made to FIG. 11, which is a view of a flowchart 160 including exemplary steps in a method to compute a balloon position matrix in the first (ICL) coordinate frame for use in the system 20 of FIG. 1. Reference is also made to FIG. 2.

As part of a calibration step, the balloon catheter 40 is placed at a given position (origin position) having a given location and a given orientation, typically outside the body, in order to register the location and orientation of the balloon catheter 40 with the proximal-electrode 52*a* at 0,0,0 cartesian coordinates and the shaft 22 pointing along the x-axis of the cartesian coordinate system. The balloon catheter 40 is then moved to a new position in the body at which point ICL and ACL positions are computed. Processing of the ICL positions is described with reference to FIG. 11 and processing of the ACL positions is described with reference to FIG. 12. Cartesian coordinates are used by way of example, and any suitable coordinate system may be used.

The processing circuitry 41 (FIG. 1) is configured to receive (block 162) ICL positions (i.e., position coordinates in the ICL coordinate frame). The ICL positions include the positions of the ten ablation electrodes 55 with an (x,y,z) coordinate for each ablation electrode 55.

The processing circuitry 41 is configured to find (block 164): a plane defined by the ICL positions of the ablation electrodes 55; and a center of a circle defined by the ICL positions of the ablation electrodes 55 using any suitable plane and circle best-fit method, respectively. Alternatively, the center of the circle defined by the ICL positions of the ablation electrodes 55 may be computed by averaging the ICL positions of the ablation electrodes 55. The processing circuitry 41 is configured to translate (block 166) the found center of the found plane to 0,0,0 coordinates without rotating the found plane.

The processing circuitry 41 is configured to receive (block 168) a model of the balloon catheter 40 with the proximal-electrode 52a at the origin position with coordinates 0,0,0. The processing circuitry 41 is configured to translate (block 170) a plane of the model so that a center of the ablation electrodes of the model is aligned with 0,0,0 coordinates instead of the proximal-electrode 52a being at the origin position with coordinates 0,0,0 without rotating the plane of the model.

Now the center of the plane defined by the ablation electrodes 55 of the balloon catheter 40 and the center of the plane defined by the ablation electrodes 55 of the balloon model are both at 0,0,0 coordinates. The processing circuitry 41 is configured to compute the rotation of the balloon by finding the rotation between the two planes, thus finding (block 172) the balloon rotation matrix $R_{ICL-scl}$ in the ICL coordinate frame.

The above computed balloon rotation matrix includes an element of scaling as the ICL positions are scaled according to ICL technology. The processing circuitry 41 is configured to find (block 174) the balloon rotation matrix without scaling giving:

$$R_{ICL} = V \begin{bmatrix} 1 & 0 & 0 \\ 0 & 1 & 0 \\ 0 & 0 & Det[V \cdot U^T] \end{bmatrix} U^T$$

where $[U,S,V]=svd(R_{ICL-scl})$, $Det[V \cdot U^T]$ is the determinant of $[V \cdot U^T]$, and for an m×n matrix M, there exists a factorization, called a 'singular value decomposition' of M, of the form $M=U*S*V^T$, where U is an m×m unitary matrix (orthogonal matrix), S is a diagonal m×n matrix with non-negative real numbers on the diagonal, V is an n×n unitary matrix and $V^T$ is the conjugate transpose of V. The diagonal entries of S are known as the singular values of M. A common convention is to list the singular values in descending order. In some embodiments, the diagonal matrix, S, may be uniquely determined by M. In the special, yet common, case when M is an m×m real square matrix with a positive determinant, U, $V^T$, and S are real m×m matrices as well. S may be regarded as a scaling matrix, and U, $V^T$ may be viewed as rotation matrices. Thus, the expression U, S, $V^T$ can be intuitively interpreted as a composition of three geometrical transformations including: a rotation or reflection; a scaling; and another rotation or reflection, respectively.

The processing circuitry 41 is configured to receive (block 176) an ICL location $[X^{ICL}, Y^{ICL}, Z^{ICL}]$ of the proximal-electrode 52a at the new position of the balloon catheter 40 in the body. The ICL location of the proximal-electrode 52a is used in finding a balloon ICL position matrix as the proximal-electrode 52a is substantially at the same position as the magnetic sensor 50 (of the balloon catheter 40), which is used in computing a balloon ACL position matrix described in more detail with reference to FIG. 12. The location of the proximal-electrode 52a provides a translation vector $\vec{P}_{ICL}$ of the proximal-electrode 52a from the origin of 0,0,0 to the current position of the proximal-electrode 52a.

The processing circuitry 41 is configured to find (block 178) the balloon ICL position matrix, $M_{ICL}$, for rotation and translation based on $R_{ICL}$ and the ICL translation vector $\vec{P}_{ICL}=[X^{ICL}, Y^{ICL}, Z^{ICL}]$ of the proximal-electrode 52a as follows:

$$M_{ICL} = \begin{bmatrix} [ & & ] & X^{ICL} \\ [ & R_{ICL} & ] & Y^{ICL} \\ [ & & ] & Z^{ICL} \\ 0 & 0 & 0 & 1 \end{bmatrix}$$

Figure 12:
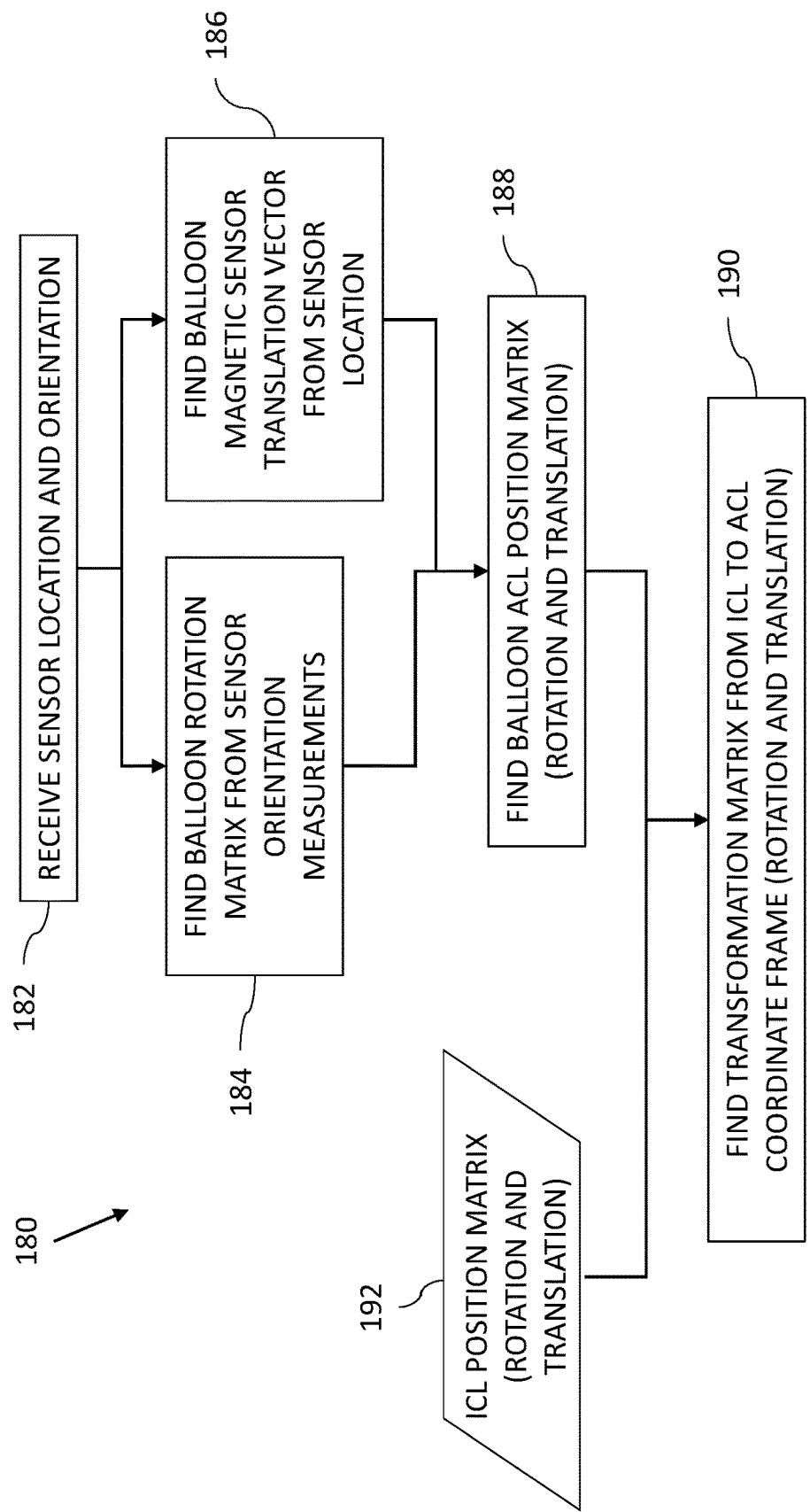
FIG. 12 is a view of a flowchart including exemplary steps in a method to compute a transformation matrix for use in the system of FIG. 1.

Reference is now made to FIG. 12, which is a view of a flowchart 180 including exemplary steps in a method to compute a transformation matrix for use in the system 20 of FIG. 1. Reference is also made to FIG. 2.

The processing circuitry 41 is configured to receive (block 182) a position (location and orientation) of the magnetic sensor 50 of the balloon catheter 40 at a position (which is the same position used to compute the ICL values with reference to FIG. 11) in the second (ACL) coordinate frame.

The processing circuitry 41 is configured to find (block 184) a 3×3 balloon rotation matrix $R_{ACL}$ from the orientation of the magnetic sensor 50 received in the step of block 182 in the second (ACL) coordinate frame.

The processing circuitry 41 is configured to a find (block 186) a balloon magnetic sensor translation vector $\vec{P}_{ACL}=[X^{ACL}, Y^{ACL}, Z^{ACL}]$ of the magnetic sensor 50 in the second (ACL) coordinate frame from the location data received in the step of block 182.

The processing circuitry 41 is configured to find (block 188) a balloon ACL position matrix, $M_{ACL}$, including rotation and translation from $R_{ACL}$ and $\vec{P}_{ACL}=[X^{ACL}, Y^{ACL}, Z^{ACL}]$ as follows:

$$M_{ACL} = \begin{bmatrix} [ & & ] & X^{ACL} \\ [ & R_{ACL} & ] & Y^{ACL} \\ [ & & ] & Z^{ACL} \\ 0 & 0 & 0 & 1 \end{bmatrix}$$

The processing circuitry 41 is configured to find (block 190) a transformation matrix $T_{ICL-ACL}$ from the ICL to ACL coordinate frame (with a rotation and translation element) based on performing an operation with the ICL position matrix $M_{ICL}$ and the ACL position matrix $M_{ACL}$. The process of block 190 is now described in more detail below.

A rotation transformation matrix $R_{ICL-ACL}$, which provides a rotational transformation from ICL orientations to ACL orientations, is defined below as follows:

$$R_{ACL}=R_{ICL-ACL}*R_{ICL}$$

$$R_{ICL-ACL}=R_{ACL}*R_{ICL}^{-1}$$

The translation between the ICL and ACL coordinate frame of the proximal-electrode 52a is given by:

$$\vec{P}_{ICL-ACL}=\vec{P}_{ACL}-\vec{P}_{ICL}=[X^{ICL}-X^{ACL}, Y^{ICL}-Y_{ACL}, Z^{ICL}-Z^{ACL}]=[X^{ICL-ACL}, Y^{ICL-ACL}, Z^{ICL-ACL}]$$

The transformation matrix which transforms from the ICL to the ACL coordinate frame is a 4×4 matrix, includes a rotation and translation element as follows:

$$T_{ICL-ACL} = \begin{bmatrix} [ & & ] & X^{ICL-ACL} \\ [ & R_{ICL-ACL} & ] & Y^{ICL-ACL} \\ [ & & ] & Z^{ICL-ACL} \\ 0 & 0 & 0 & 1 \end{bmatrix}$$

The transformation is used to transfer any suitable probe visualization from the ICL to ACL coordinate frame based on $T_{ICL-ACL} * P_{ICL} = P_{ACL}$, where $P_{ICL}$ is the position matrix in the ICL coordinate frame and $P_{ACL}$ is the position matrix in the ACL coordinate frame.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical probe tracking system, comprising:
a plurality of body surface electrodes configured to be applied to a skin surface of a living subject;
a probe, configured to be inserted into a body of the living subject, comprising probe electrodes and a magnetic field sensor;
a magnetic field generator configured to generate a magnetic field within the body of the living subject;
a display; and
processing circuitry configured to:
measure electrical currents between the body surface electrodes and the probe electrodes within the body, respectively;
compute first position coordinates of the probe in a first coordinate frame responsively to a distribution of a first multiplicity of the electrical currents;
receive magnetic position signals from the magnetic field sensor in response to the magnetic field;
render to the display an initial three-dimensional (3D) representation of the probe in the first coordinate frame according to the first position coordinates and then compute a current-position map (CPM) between a distribution of a second multiplicity of the electrical currents and the magnetic position signals with respect to a second coordinate frame defined by the magnetic field generator;
find a transformation between the first and second coordinate frames;
apply the transformation to the first position coordinates yielding second position coordinates of the probe in the second coordinate frame; and
render to the display a modified 3D representation of the probe in the second coordinate frame according to the second position coordinates, wherein said modified 3D representation is displayed after finding the transformation,
wherein the transformation includes a rotation and a translation element, the first position coordinates including a location and an orientation, the second position coordinates having a location and an orientation, the processing circuitry being configured to render the modified 3D representation of the probe based on the location and the orientation of the second position coordinates,
wherein the probe includes a balloon catheter having a shaft, an inflatable balloon fitted at a distal end of the shaft, multiple electrodes of the probe disposed on the inflatable balloon, the magnetic field sensor being disposed at a proximal end of the shaft, the processing circuitry being configured to: find a balloon rotation matrix from a rotation between a first plane defined by the multiple electrodes and a second plane defined by electrodes in a balloon catheter model; and find the transformation based on the balloon rotation matrix, and
wherein the processing circuitry is adapted to apply a first electrical signal-based method, wherein the first electrical signal-based method is Independent Current Location (ICL), resulting in a calculation of the location of the probe in the first coordinate frame which is an ICL coordinate frame;
wherein the processing circuitry is also adapted to apply a second electrical signal-based method, wherein the second electrical signal-based method is Active Current Location (ACL), wherein the processing circuitry correlates the distribution of measured currents associated with the probe electrodes with the CPM, resulting in the calculation of the location of the probe in the second coordinate frame which is an ACL coordinate frame; and
wherein the transformation is between the ICL coordinate frame and the ACL coordinate frame.

2. The system according to claim 1, wherein the processing circuitry is configured to: render the initial 3D representation of the probe according to the first coordinate frame prior to computation of the CPM; and render the modified 3D representation of the probe according to the second coordinate frame after computation of the CPM.

3. The system according to claim 1, wherein the processing circuitry is configured to render a further modified 3D representation of the probe according to third position coordinates located in the volume based on at least any one or more of the following: a magnetic position derived from the CPM based on a distribution of a third multiplicity of the electrical currents; and from the magnetic field detected by the magnetic field sensor.

4. A medical probe tracking method, comprising:
applying a plurality of body surface electrodes to a skin surface of a living subject;
inserting a probe comprising probe electrodes and a magnetic field sensor into a body of the living subject;
generating, by a magnetic field generator, a magnetic field within the body of the living subject;
measuring electrical currents between the body surface electrodes and the probe electrodes within the body, respectively;
computing first position coordinates of the probe in a first coordinate frame responsively to a distribution of a first multiplicity of the electrical currents;
receiving magnetic position signals from the magnetic field sensor in response to the magnetic field;
rendering to the display an initial three-dimensional (3D) representation of the probe in the first coordinate frame according to the first position coordinates and then compute a current-position map (CPM) between a distribution of a second multiplicity of the electrical currents and the magnetic position signals with respect to a second coordinate frame defined by the magnetic field generator;

finding a transformation between the first and second coordinate frames;

applying the transformation to the first position coordinates yielding second position coordinates of the probe in the second coordinate frame; and rendering to the display a modified 3D representation of the probe in the second coordinate frame according to the second position coordinates, wherein said modified 3D representation is displayed after finding the transformation wherein the transformation includes a rotation and a translation element, the first position coordinates including a location and an orientation, the second position coordinates having a location and an orientation, the rendering of the modified 3D representation including rendering the modified 3D representation of the first probe based on the location and the orientation of the second position coordinates, wherein the probe includes a balloon catheter having a shaft, an inflatable balloon fitted at a distal end of the shaft, multiple electrodes of the probe electrodes on the inflatable balloon, the magnetic field sensor being disposed at a proximal end of the shaft, the method further comprising: finding a balloon rotation matrix from a rotation between a first plane defined by the multiple electrodes and a second plane defined by electrodes in a balloon catheter model; and finding the transformation based on the balloon rotation matrix, and applying a first electrical signal-based method, wherein the first electrical signal-based method is Independent Current Location (ICL), resulting in a calculation of the location of the probe in the first coordinate frame which is an ICL coordinate frame;

applying a second electrical signal-based method, wherein the second electrical signal-based method is Active Current Location (ACL), wherein the processing circuitry correlates the distribution of measured currents associated with the probe electrodes with the CPM, resulting in the calculation of the location of the probe in the second coordinate frame which is an ACL coordinate frame; and wherein the transformation is between the ICL coordinate frame and the ACL coordinate frame.

5. The method according to claim 4, wherein the rendering of the initial 3D representation is performed prior to the computing of the CPM and the render of the modified 3D representation is performed after the computing of the CPM.

6. The method according to claim 4, further comprising rendering a further modified 3D representation of the probe according to third position coordinates located in the volume based on at least any one or more of the following: a magnetic position derived from the CPM based on a distribution of a third multiplicity of the electrical currents; and from the magnetic field detected by the magnetic field sensor.

* * * * *